United States Patent [19]
DeCamp et al.

[11] Patent Number: 5,792,099
[45] Date of Patent: Aug. 11, 1998

[54] SYRINGE AND CANNULA FOR INSERTION OF VISCOELASTIC MATERIAL INTO AN EYE AND METHOD OF USING SAME

[76] Inventors: Dennis DeCamp, 228 E. Center St., #104, Covina, Calif. 91723; David Haffner, 24681 Via San Fernando, Mission Viejo, Calif. 92692

[21] Appl. No.: 389,814

[22] Filed: Feb. 14, 1995

(Under 37 CFR 1.47)

[51] Int. Cl.⁶ .............. A61M 31/00; A61M 5/00
[52] U.S. Cl. .............. 604/51; 604/117; 604/272; 604/239; 604/240; 604/241
[58] Field of Search .............. 604/117, 187, 604/181, 188, 191, 218, 239, 240, 241, 242, 243, 264, 272, 274, 294, 295, 296, 297, 298, 300, 289, 290, 273, 22, 51, 283; 128/898; 433/89, 90; 606/166–167, 185

[56] References Cited

U.S. PATENT DOCUMENTS

| | | | |
|---|---|---|---|
| 4,759,746 | 7/1988 | Straus | 604/272 |
| 4,878,904 | 11/1989 | Callaway | 604/272 |
| 5,002,535 | 3/1991 | Gross | 604/272 |
| 5,284,476 | 2/1994 | Koch | 604/272 |
| 5,554,133 | 9/1996 | Haffner et al. | 604/187 |

*Primary Examiner*—Ronald K. Stright, Jr.
*Attorney, Agent, or Firm*—Walter A. Hackler

[57] ABSTRACT

A syringe for insertion of viscoelastic material into an eye includes a syringe body having an end with an opening therein and a pseudoplastic viscoelastic material disposed in the syringe body. The viscoelastic material is pseudoelastic and may have an initial viscosity of between about 5,000 and about 60,000 centipoise. Correspondingly a cannula is provided which includes a needle having a dispensing orifice on one end thereof and a first portion of between about 23- and about 18-gauge tubing, distal from the dispensing orifice and a second portion of between about 30- and about 23-gauge tubing, proximal to the dispensing orifice. Additionally a housing is provided for attaching another end of the needle, proximal to the first portion, to the end of the syringe body. A method for dispensing the viscoelastic material includes compressing the viscoelastic material in order to force the viscoelastic material out of the syringe and passing the forced viscoelastic material through a large gauge portion of a needle to establish flow of the viscoelastic material. Thereafter the forced viscoelastic material is passed through a narrow gauge portion of the needle for dispensing through an orifice therein.

15 Claims, 2 Drawing Sheets

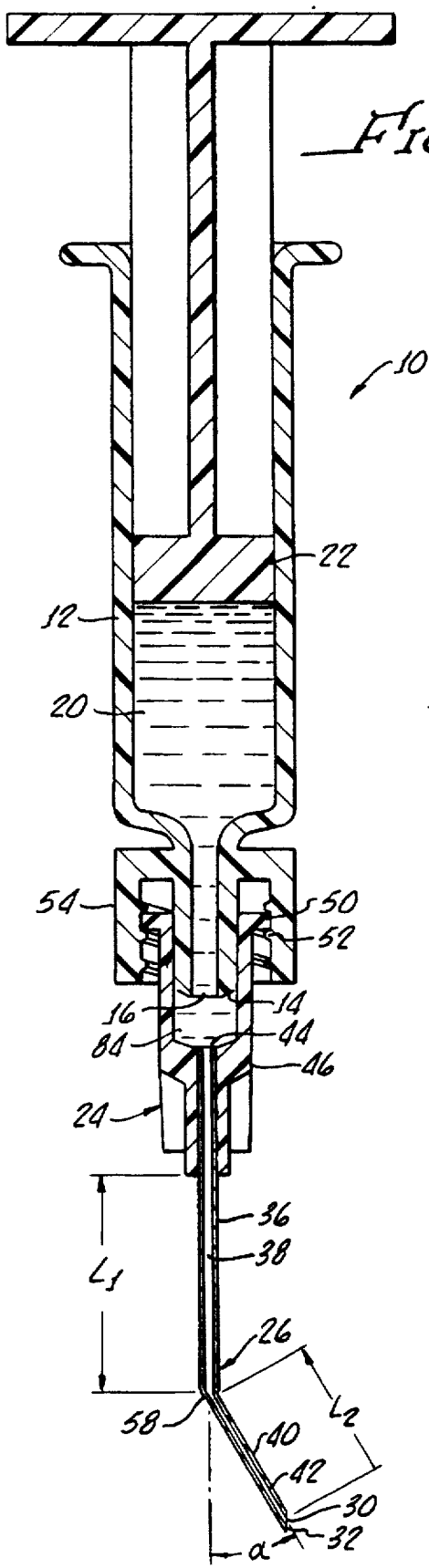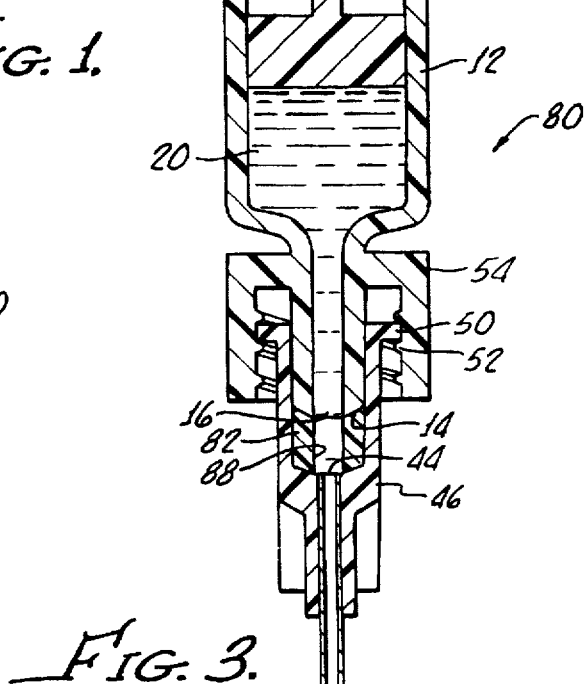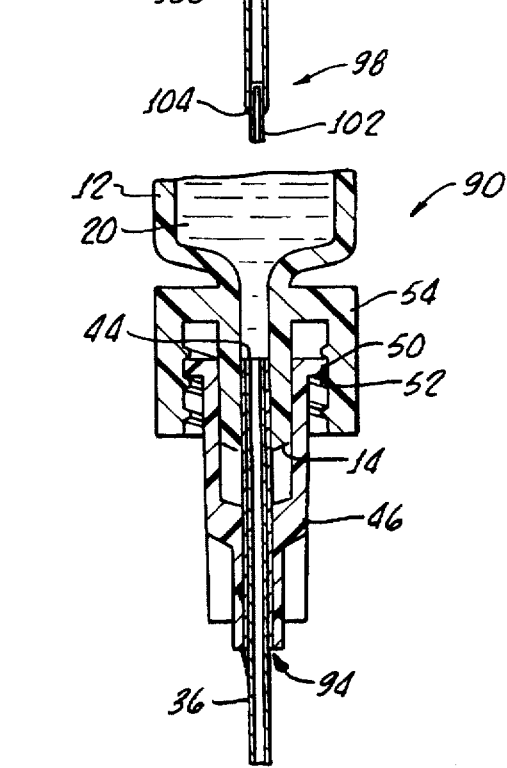

Fig. 2.
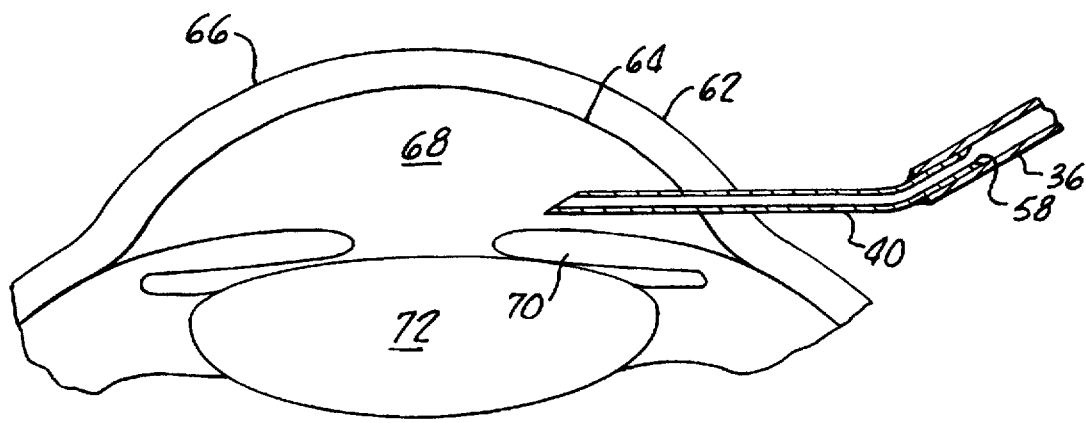
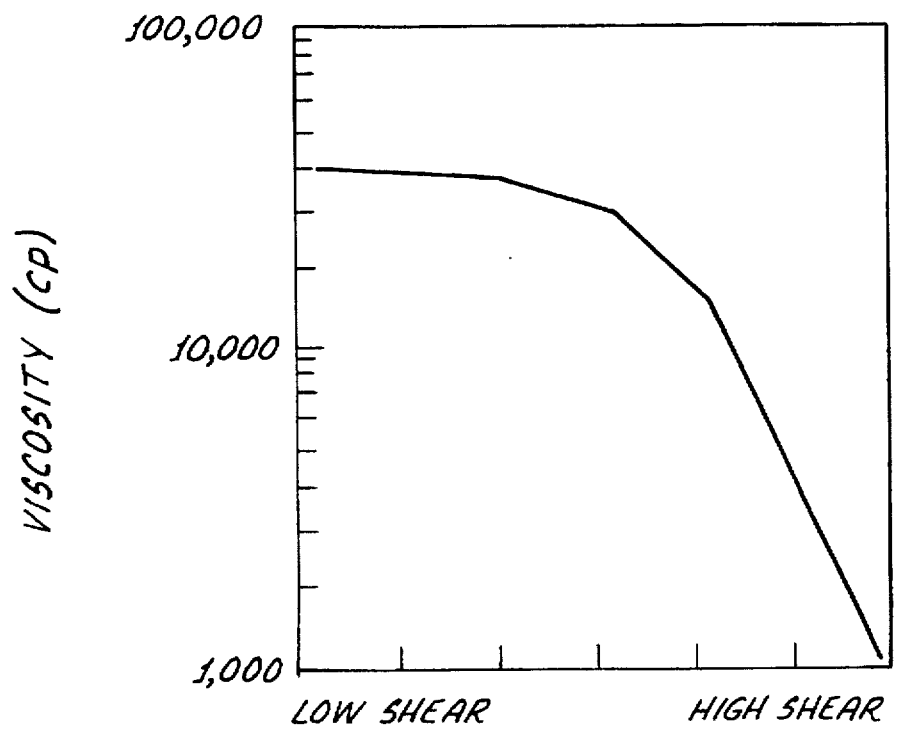
Fig. 5.

SYRINGE AND CANNULA FOR INSERTION OF VISCOELASTIC MATERIAL INTO AN EYE AND METHOD OF USING SAME

The present invention generally relates to surgical syringes and, more particularly, is directed to syringes and cannulas suitable for insertion into an ocular cavity during ophthalmic surgery.

In many ophthalmic surgical procedures, such as, for example, intraocular lens implantation, cataract surgery, and retinal detachment repair, a viscoelastic gel-like composition is utilized to fill the chambers of the eye in order to protect sensitive tissues, in particular, the cornea endothelium from trauma.

A number of compositions have been utilized, which include solutions of hyaluronic acid, chondroitin sulfate and methylcellulose. These compositions are viscoelastic gel-like and commonly referred to as viscoelastic materials.

Further the classification of viscoelastic materials utilized in regulating or maintaining humoral pressure during ophthalmic surgery include adhesive viscoelastic, such as Viscoat® or cohesive viscoelastic, such as Healon®.

Adhesive viscoelastic materials are effective in coating the endothelium and further resist washout during surgical procedures, such as phaco surgery, which includes the irrigation of the eye having a chamber with balanced saline solution. While adhesive viscoelastic materials are effective for coating the endothelium, subsequent removal thereof is difficult because of their adhesive nature. Further, such viscoelastic materials are not cohesive in that they do not tend to maintain integrity but preferably adhere to eye surfaces. This is particularly troublesome in conventional eye surgery in which viscoelastic material is aspirated at the completion of the surgical procedure.

It is well known that aspiration of the viscoelastic material is necessary due to the fact that retained viscoelastic material within the eye causes elevated intraocular pressure and therefore a complete removal of the viscoelastic material at the end of the operation may lead to increased intraocular pressure.

A more desirable viscoelastic material for eye surgery is one which sticks, or adheres, to the tissues of the eye with greater adherence than it sticks to itself. Thus, this type of viscoelastic is not easily dislodged by turbulence.

Yet another problem associated with any of the viscoelastic materials is the ease of insertion of the viscoelastic material into the ocular cavity. This is typically done through the use of a syringe/cannula combination, which includes a needle having a piercing end for entering the ocular cavity through which viscoelastic material is forced by means of a conventional-type syringe. It should be appreciated that the needle utilized in such an operation should be of as small a gauge as possible in order to reduce trauma.

This requirement imposes further constraints on the type of viscoelastic material suitable for injection. This limitation then is manifest by the viscosity of the viscoelastic material. The result is that otherwise suitable viscoelastic materials may not be preferred for insertion into an eye through an acceptable gauge needle in view of the fact that the characteristic viscosity of the material limits its flow through preferred needle gauges either by limited fluid flow or by pressure which must be developed to obtain a desirable fluid flow through the needle.

The present invention is directed to a syringe/cannula for taking advantage of pseudoplastic properties of certain viscoelastic materials in order to pass the viscoelastic material through narrow gauge needles most suitable for introducing the viscoelastic material into an eye.

SUMMARY OF THE INVENTION

A syringe in accordance with the present invention for insertion of viscoelastic material into an eye generally includes a syringe body having an end with an opening therein. Incorporated within the syringe body is a pseudoplastic viscoelastic material having a viscosity of between about 5,000 and 60,000 centipoise. A cannula is provided which includes a needle comprising a first large diameter section and a second smaller diameter section with the second section connected to an end of the first section and a dispensing orifice being located at the end of the second section opposite or distal the connection of the two sections. The opposite or proximal end of the first section of the needle including means for attachment to the syringe body.

Because the needle is comprised of two portions, the first being of a larger gauge than the second, force exerted on the viscoelastic material for dispensing same from the syringe through the cannula begins the flow of the viscoelastic material, which is pseudoplastic, through the larger diameter first portion of the needle. Once this flow is established, because of the pseudoplastic nature of the viscoelastic material, it can be forced through the smaller diameter, or gauge, second portion of the needle for insertion into an eye when the second portion of the needle is properly positioned in an ocular cavity.

Thus, the present invention has, as an advantage, a portion of a needle of very narrow gauge suitable for insertion into an ocular cavity, while at the same time providing a relatively larger diameter, or gauge, portion of the needle for accepting and establishing flow of the viscoelastic material therein.

The use of the uniform gauge needle suitable for insertion into an eye does not enable the use of more viscous viscoelastic material since flow is difficult to initially establish in a narrow gauge needle.

The relative gauges of the different portions of the needle is of course dependent upon the initial viscosity of the viscoelastic material.

More particularly, in accordance with the present invention, when the initial viscosity of the viscoelastic materia is about 40,000 centipoise, the first portion of the needle is formed from about 19-gauge tubing and the second portion is formed from about 26-gauge tubing. As hereinabove noted, the gauges of the tubing are dependent upon the initial viscoelastic material and the ranges thereof are hereinabove set forth.

More specifically, this range, in accordance with the present invention, may include a cannula with a length of the first portion of the needle between about 0.25 and about 0.5 inch and the length of the second portion of the needle being between about 0.25 and about 0.5 inch. Preferably, the length of each of the first and the second portions of the needle is about 0.375 inch.

If the syringe of the present invention is of conventional design, the means for attaching the needle thereto may include a conical housing disposed coaxially on the first portion of the needle, with the housing having a hollow interior sized to fit onto the end of the syringe body. In this instance, a void is established between the end of the needle and the end of the syringe body which, in accordance with the present invention, may be filled by means of a plug which includes a bore therethrough aligned with the end of the opening in the syringe body.

The purpose of the plug in this instance is to avoid waste of the viscoelastic material into this void which is not recoverable. Lost quantities of the viscoelastic material are of great importance since the size of a typical syringe supplying the viscoelastic material is only between about 0.5 and 1 milliliter.

Alternatively, the means for attaching the needle to the syringe body may include a conical housing disposed coaxially on the first portion, as hereinabove set forth, with the void established between the first portion of the needle and the end of the syringe body. However, in this embodiment, the conical housing is disposed at a point along the first portion to enable contact of the end of the needle with the end of the syringe body directly when the hollow interior is fit onto the end of the syringe body end.

Another feature of the present invention is established by the difference in the diameters of the second and first portion of the needle, particularly when the first and second needle portions are coaxial. In this case, a shoulder is defined by a diameter difference between the first and second portions which enables visual determination of the amount that the second portion of the needle is inserted into an eye.

Alternatively, a second portion of the needle may be disposed at an angle to the first portion of the needle.

While not necessary for establishing the flow characteristics provided by the present invention, the point of inflection between the first and second portions may occur at a shoulder which is defined by a diameter difference between the first and second portions of the needle.

More specifically, the present invention comprises a cannula for use with a conventional syringe which includes a needle comprising a first large diameter section and a second smaller diameter section with the second section connected to an end of the first section and a dispensing orifice being located at the end of the second section opposite or distal the connection of the two sections. The opposite or proximal end of the first section of the needle having the attachment means thereon.

The present invention further encompasses a method of dispensing a viscoelastic material, in particular a pseudoplastic viscoelastic material, through a needle having a gauge portion thereof suitable for insertion into an eye. The method of the present invention includes providing a supply of viscoelastic material, for example, in a syringe, and compressing the viscoelastic material in the syringe in order to force the viscoelastic material out an opening in the syringe.

The method further encompasses passing the forced viscoelastic material through a large gauge portion of a needle in order to establish a flow and thereafter passing the forced viscoelastic material through a small gauge portion of the needle for dispensing through an orifice therein.

BRIEF DESCRIPTION OF THE DRAWINGS

The advantages and features of the present invention will appear from the following description when considered in conjunction with the accompanying drawings in which:

FIG. 1 is a cross-sectional view of the present invention generally showing a syringe in a cannula with a needle having two portions of different diameters attached thereto;

FIG. 2 is a representation of the syringe/cannula shown in FIG. 1 as it may be utilized for introducing a viscoelastic material into an eye during surgery;

FIG. 3 is a cross-sectional view of one embodiment of the present invention utilizing a plug for adapting the cannula of the present invention to a conventional syringe;

FIG. 4 is a cross-sectional view of an alternative embodiment of the present invention with the cannula disposed on a needle for enabling direct contact of the needle with an opening in the syringe; and FIG. 5 is a plot of viscosity vs. shear for a viscoelastic suitable for use in the present invention.

DETAILED DESCRIPTION

Turning now to FIG. 1, there is shown a syringe 10 in accordance with the present invention which generally includes a syringe body 12, which may be of a conventional design, having an end 14 with an opening 16 therein.

A viscoelastic material 20 may be disposed within the syringe body 12 and a piston 22 utilized to compress the viscoelastic material and force it out of the syringe 10. The viscoelastic material may be a sodium hyaluronate solution such as Vitrax® available from Allergan, Inc. and having a viscosity of between about 5,000 and about 60,000 centipoise. Importantly, the viscoelastic material is pseudoplastic and as hereinabove noted, the cannula of the present invention is particularly suited for insertion of such viscoelastic material into an eye due to the structural features herein described.

A cannula 24 is provided which includes a needle 26 having a dispensing orifice 30 on a first end 32.

Importantly, the needle 26 includes a first large diameter portion, or section, 36 (with lumen 38) and second smaller diameter portion, or section, 40 (with lumen 42) with the second section 40 connected to an end 58 of the first section 36 and the dispensing orifice 30 being located at the end 32 of the second section 38 opposite or distal the first section end 58.

The opposite or proximal end of the first section 36 of the needle 26 having a conical housing 46 thereon for providing a means for attaching the needle 26 to the end 14 of the syringe body 12.

The conical housing 46 may be formed of any suitable material and attached in a conventional manner to the first portion 36 of the needle 26. The housing 46 includes an outwardly extending flange 50 which engages threads 52 in a depending portion 54 in a conventional manner.

As will be hereinafter discussed in greater detail in connection with the pseudoplasticity of the viscoelastic, the first portion 36 of the needle 26 may be formed from between about 18- and 23-gauge tubing, and the second portion 40 may be formed from between about 23- and 30-gauge tubing. This corresponds inversely with the initial viscosity of the viscoelastic material utilized which has a range of between about 5,000 and about 60,000 centipoise.

Because of the difference in tubing sizes between the first portion 36 and the second portion 40, a shoulder 58 is established therebetween. In addition, the second portion 40 may be disposed at an angle, alpha, as shown in FIG. 1. This angle may vary between 0° and 60° and preferably is between approximately 25° and 35°.

As a specific example, with an initial viscosity of viscoelastic material 20 of about 40,000 centipoise. The first portion 36 is preferably formed from about 19-gauge tubing, and the second portion 40 is formed from preferably 26-gauge tubing. A length $L_1$ of the first portion 36 may vary between 0.25 and 0.5 inch and a length $L_2$ of the second portion 40 may also vary between about 0.25 and 0.5 inch, with the preferred embodiment being 0.375 inch for the first portion 36 and the second portion 40.

The advantage of the angular disposition between the first portion 36 and the second portion 40 is illustrated in FIG. 2 wherein the second portion 40 is shown inserted through a conjunctiva 62 and a cornea 64 of an eye 66 into a cavity 68 over an iris 70 and lens 72.

Turning to FIG. 3, another embodiment 80 of the present invention includes, as part of the means for attaching the end 44 to the syringe body, a plug 82 for filling a void 84 (see FIG. 1) which is established between the end 44 of needle 26 and the end 14 of the syringe body 12.

The plug 82 includes a bore 88 therethrough which is aligned with the needle end and an opening 16. This arrangement provides for minimizing the loss of viscoelastic material 20 into the void 84, which may occur if plug 82 were not present. This, of course, results in the savings of viscoelastic material which may be irretrievably lost in the void 84. As noted hereinabove, this situation arises when the conventional type of syringe is utilized in combination with the cannula 24.

Another alternative embodiment 90 in accordance with the present invention is shown in FIG. 4. It should be appreciated that common elements as shown in the present application are identified by identical character references.

In the embodiment 90 shown in FIG. 4, the housing 46 is disposed at a point 94 on the first portion 36 for enabling direct contact with, or insertion into, the syringe body end 14 by the end 44 of the first portion 36. In this manner, the void 84 established by coupling the housing 46 with the depending portion 54 of the syringe body 12 is bypassed in order to provide direct fluid communication from the syringe body 12 into the first portion 36 of the needle 26.

Returning to FIG. 3, the embodiment 80 therein shown includes a straight needle 98 which includes a large diameter first portion 100 and a small diameter second portion 102 in a coaxial relationship with a shoulder 104 established by a difference in the diameters of the first portion 100 and second portion 102, which provides a means for enabling visual determination of an amount that the small diameter portion 102 is inserted into an eye. That is, because there is a visual mark on the needle 98 established by the shoulder 104, the depth of penetration of the second portion 102, or insertable portion, into an eye can be discerned.

Of great importance to the present invention is the fact that the needle 26, 98 is comprised of two portions 36, 40 and 100 and 102 respectively, which have decreasing diameter. This is done to optimize the physical characteristics of the ophthalmic viscoelastic material utilized, namely, sodium hyaluronate.

Sodium hyaluronate is a long, folded, ribbon-like chain of polysaccharide found naturally in soft or loose connective tissues, synovial fluid, and the aqueous and vitreous humors of the eye. It is also found in the coats of some bacteria. In its naturally occurring state, sodium hyaluronate provides tissue-stabilizing, lubricating, and shock-absorbing effects. It surrounds cells and fibers, disperses shock, and protects delicate tissues and cells from permanent deformation and injury.

In solution, the sodium hyaluronate chain twists and folds back on itself and forms a long, loose, randomly arranged spheroidal coil. As this coil attracts molecules of water, it expands and occupies a large volume of space. The ability of sodium hyaluronate to expand its molecular structure with hydration is what gives it shock-absorbing capability. Solutions of sodium hyaluronate resist flow (are viscous) and recover some of their original shape after being stretched (are elastic).

Corneal endothelial cells have been shown to have bind sites for the attachment of sodium hyaluronate, and solutions with higher molecular weight have been reported to have a greater binding affinity to these sites than solutions of lower molecular weight. The clinical significance of these binding sites and whether higher molecular weight solutions coat and protect the endothelium better than lower molecular weight solutions, however, has not been determined. The amount of hyaluronate that coats the endothelium after aspiration is determined not only by binding affinity but also by the cohesive forces that tend to keep the sodium hyaluronate as a single mass that follow itself during aspiration. Under test conditions in certain applications, high molecular weight viscoelastics, such as Healon®, have shown more cohesiveness than lower molecular weight viscoelastics, such as AMO® Vitrax®.

The term viscosity as referred to in discussions of ophthalmic viscoelastics is actually dynamic viscosity, which is thickness or resistance to flow. Dynamic viscosity is expressed in centipoise (cp). Fluids such as air, water, and chondroitin sulfate, whose viscosity is independent of shear rate (degree of movement), are referred to as Newtonian fluids. These fluids have the same viscosity even when stress is applied to them. Sodium hyaluronate solutions, however, are non-Newtonian fluids and show less resistance to flow with increasing shear rate.

The dynamic viscosity of a viscoelastic substance is not a single number but a range of numbers, varying with the temperature and shear rate at which the viscosity was measured. When shear is minimal or not present—that is, when the sodium hyaluronate polymer is at rest—it resists flow because the folded molecules are highly entangled. Thus this initial viscosity exhibits the gel-like behavior of sodium hyaluronate at rest. When shear is applied, however, the folding decreases, the extent of entanglement drops, and the viscous solution is able to flow through a syringe. The ability of sodium hyaluronate to decrease its dynamic viscosity at increasing shear rate is known as pseudoplasticity.

If the shear on the sodium hyaluronate molecule is increased, the long sodium hyaluronate chains unfold and stretch out. This makes the polymer less like a gel and more like a liquid. A further increase in shear, as when a viscoelastic is pushed through a cannula, will cause the chains to further unfold and stretch out and achieve an even thinner state. This process of transformation from a gel to a liquid is known as pseudoplasticity. Pseudoplasticity indicates the ability of a solution to reduce its viscosity when stress or shear is applied. For sodium hyaluronate, pseudoplasticity decreases with decreasing chain length.

Pseudoplasticity is an important characteristic of viscoelastics because a surgeon needs high, viscosity when the substance is stationary (no shear) in order to maintain surgical space, low viscosity when it is being injected through a cannula (high shear), and intermediate viscosity when an intraocular lens or surgical instrument must be slipped through it (intermediate shear). Pseudoplasticity of a viscoelastic also gives the surgeon "tactile feedback" during injection—that is, a feeling for the proper volume to inject and the force at which it should be injected.

The change in viscosity under shear as shown in FIG. 5 is used to advantage in the present invention for enabling viscoelastic material to be passed through a tube diameter which is suitable for insertion into an eye, which otherwise would not exempt initial flow of the viscoelastic material.

Thus, in accordance with the present invention, a method is provided which includes passing viscoelastic material through a large gauge portion of the needle to establish flow of the viscoelastic material and thereafter passing the viscoelastic material through a small gauge portion of the needle through dispensing through an orifice and into an eye.

Although there has hereinabove been described apparatus and method for the insertion of viscoelastic material into an eye, in accordance with the present invention, for the purpose of illustrating the manner in which the invention may be used to advantage, it should be appreciated that the invention is not limited thereto. Accordingly, any and all modifications, variations, or equivalent arrangements which may occur to those skilled in the art should be considered to be within the scope of the present invention as defined appended claims.

What is claimed is:

1. A method for dispensing a viscoelastic material, said method comprising the steps of:

providing a supply of viscoelastic material having an initial viscosity of about 40,000 centipoise;

compressing the viscoelastic material in a syringe in order to force the viscoelastic material out of an opening in the syringe;

passing the forced viscoelastic material through a 19-gauge portion of a needle to establish flow of the viscoelastic material; and thereafter passing the forced viscoelastic material through a 26-gauge portion of the needle for dispensing through an orifice therein.

2. A syringe for insertion of viscoelastic material into an eye, said syringe comprising:

a syringe body having an end with an opening therein;

a pseudoplastic viscoelastic material disposed in said syringe body, the viscoelastic material having an initial viscosity of about 40,000 centipoise;

a cannula including a needle having a first large diameter section and a second small diameter section with a dispensing orifice disposed on an end of the second section, the first section comprising about 19-gauge tubing and the second section comprising about 26-gauge tubing; and means for attaching the first section to the end of the syringe body.

3. The syringe according to claim 2 wherein a length of said first section is between about 0.25 and about 0.5 inch and the length of said second section is between about 0.25 and about 0.5 inch.

4. The syringe according to claim 3, wherein a length of said first section is about 0.375 inch and a length of said second section is about 0.375 inch.

5. The syringe according to claim 2 wherein said first section and said second portion are coaxial and the cannula further comprises shoulder means, defined by a diameter difference between the first section and the second portion, for enabling visual determination of an amount of the second section inserted into an eye.

6. The syringe according to claim 2 wherein said second section of the needle is disposed at an angle to the first section of the needle.

7. The syringe according to claim 2 further comprising a shoulder defined by a diameter difference between the first section and the second portion, and the second section of the needle is disposed at an angle to the first section of the needle with a point of inflection at the shoulder.

8. A syringe for insertion of viscoelastic material into an eye, said syringe comprising:

a syringe body having an end with an opening therein;

a pseudoplastic viscoelastic material disposed in said syringe body, the viscoelastic material having an initial viscosity of between about 5,000 and about 60,000 centipoise;

a cannula including a needle having a first large diameter section and a second small diameter section with a dispensing orifice disposed on an end of the second section the first section comprising tubing of between less than about 23-gauge and about 18-gauge and the second section comprising tubing of between about 30-gauge and more than about 23-gauge; and means for attaching the first section to the end of the syringe body, the means for attaching comprising a conical housing disposed coaxially on the first section with means for defining a hollow interior sized to fit onto the end of the syringe body, with a void established between the first section of the needle and the end of the syringe body and plug means for filling the void, said plug means having a bore therethrough aligned with the syringe body end opening.

9. A syringe for insertion of viscoelastic material into an eye, said syringe comprising:

a syringe body having an end with an opening therein;

a pseudoplastic viscoelastic material disposed in said syringe body the viscoelastic material having an initial viscosity of between about 5,000 and about 60,000 centipoise;

a cannula including a needle having a first large diameter section and a second small diameter section with a dispensing orifice disposed on an end of the second section the first section comprising tubing of between less than about 23-gauge and about 18-gauge and the second section comprising tubing of between about 30-gauge and more than about 23-gauge; and means for attaching the first section to the end of the syringe body, the means for attaching comprising a conical housing disposed coaxially on the first section with means for defining a hollow interior sized to fit onto the end of the syringe body, with a void established between the first section and the end of the syringe body, said conical housing being disposed at a point along the first section to enable contact of the first section with the end of the syringe body as the hollow interior is fit onto the end of the syringe body.

10. A cannula for insertion of viscoelastic material into an eye said cannula comprising:

a needle having a first large diameter section and a second small diameter section with a dispensing orifice disposed on the second section; and means for attaching the first section to an end of a conventional syringe to establish fluid communication therebetween, the means for attaching comprising a conical housing disposed coaxially on the first section with means for defining a hollow interior, said hollow interior being sized to fit onto the end of the conventional syringe, with a void established between the first section and the end of the conventional syringe, and plug means for filling the void, said plug means having a bore therethrough aligned with the first section and an opening in the conventional syringe.

11. The cannula according to claim 10 wherein said first section of the needle is between about 18 and about 23 gauge, and said second section is between about 26 and about 30 gauge.

12. The cannula according to claim 11 wherein said first section of the needle is about 19 gauge and said second section is about 26 gauge.

13. The cannulas according to claim 12 wherein said second section is disposed at an angle to the first section.

14. The cannula according to claim 10 wherein said first section and said second section are coaxial and the cannula further comprises shoulder means, defined by a diameter difference between the first section and the second section, for enabling visual determination of an amount of the second section inserted into an eye.

15. The cannula according to claim 10 further comprising a shoulder defined by a diameter difference between the first section and the second section, and the second section of the needle is disposed at an angle to the first section of the needle with a point of inflection at the shoulder.

\* \* \* \* \*